US00RE48302E

(19) United States
(12) Reissued Patent
Goupil et al.

(10) Patent Number: US RE48,302 E
(45) Date of Reissued Patent: *Nov. 10, 2020

(54) EMBOLIC COMPOSITIONS

(71) Applicant: BioCure, Inc., Peachtree Corners, GA (US)

(72) Inventors: Dennis Goupil, Orchard Park, NY (US); Hassan Chaouk, Jacksonville, FL (US); Troy Holland, Suwanee, GA (US); Bruktawit Asfaw, Mableton, GA (US); Stephen D. Goodrich, Longmont, CO (US); Lucas Latini, Lodi, NY (US)

(73) Assignee: BioCure, Inc., Peachtree Corners, GA (US)

( * ) Notice: This patent is subject to a terminal disclaimer.

(21) Appl. No.: 16/045,954

(22) Filed: Jul. 26, 2018

Related U.S. Patent Documents

Reissue of:
(64) Patent No.: 8,221,735
Issued: Jul. 17, 2012
Appl. No.: 12/386,828
Filed: Apr. 23, 2009

U.S. Applications:
(60) Continuation of application No. 14/334,294, filed on Jul. 17, 2014, now Pat. No. Re. 47,121, which is an application for the reissue of Pat. No. 8,221,735, which is a division of application No. 10/465,497, filed on Jun. 19, 2003, now abandoned, which is a division of application No. 09/804,963, filed on Mar. 13, 2001, now Pat. No. 6,676,971.

(60) Provisional application No. 60/254,697, filed on Dec. 11, 2000, provisional application No. 60/188,975, filed on Mar. 13, 2000.

(51) Int. Cl.

| | |
|---|---|
| ***A61K 31/765*** | (2006.01) |
| ***A61L 27/34*** | (2006.01) |
| ***A61L 27/16*** | (2006.01) |
| ***A61L 24/06*** | (2006.01) |
| ***A61L 24/00*** | (2006.01) |
| ***A61B 17/12*** | (2006.01) |
| ***A61L 31/04*** | (2006.01) |
| ***A61L 31/10*** | (2006.01) |
| ***A61L 27/52*** | (2006.01) |
| ***A61L 29/04*** | (2006.01) |
| ***C08L 51/00*** | (2006.01) |
| ***C08F 261/04*** | (2006.01) |
| ***C08L 51/08*** | (2006.01) |
| ***A61L 29/08*** | (2006.01) |
| ***C08F 290/12*** | (2006.01) |
| ***C08F 271/02*** | (2006.01) |
| ***C08F 8/30*** | (2006.01) |

(52) U.S. Cl.
CPC ..... *C08L 51/003* (2013.01); *A61B 17/12022* (2013.01); *A61B 17/12122* (2013.01); *A61B 17/12186* (2013.01); *A61L 27/34* (2013.01); *A61L 27/52* (2013.01); *A61L 29/085* (2013.01); *A61L 31/048* (2013.01); *A61L 31/10* (2013.01); *C08F 8/30* (2013.01); *C08F 261/04* (2013.01); *C08F 271/02* (2013.01); *C08F 290/12* (2013.01); *C08L 51/08* (2013.01)

(58) Field of Classification Search
CPC ..... C08L 51/003
See application file for complete search history.

(56) References Cited

U.S. PATENT DOCUMENTS

| | | | |
|---|---|---|---|
| 5,047,055 | A | 9/1991 | Bao et al. |
| 5,202,352 | A | 4/1993 | Okada et al. |
| 5,278,202 | A | 1/1994 | Dunn |
| 5,344,452 | A | 9/1994 | Lemperle |
| 5,410,016 | A | 4/1995 | Hubbell |
| 5,508,317 | A | 4/1996 | Muller |
| 5,514,379 | A | 5/1996 | Weissleder |
| 5,529,914 | A | 6/1996 | Hubbell et al. |
| 5,709,854 | A | 1/1998 | Griffith-Cima |
| 5,823,198 | A | 10/1998 | Jones et al. |
| 5,833,652 | A | 11/1998 | Preissman et al. |
| 5,844,016 | A | 12/1998 | Sawhney et al. |
| 5,879,713 | A | 3/1999 | Roth |
| 5,902,599 | A | 5/1999 | Anseth |
| 5,925,683 | A | 7/1999 | Park |

(Continued)

FOREIGN PATENT DOCUMENTS

| | | |
|---|---|---|
| EP | 730 847 | 9/1996 |
| WO | WO 92/21327 | 12/1992 |

(Continued)

OTHER PUBLICATIONS

"Syringe" from Wikipedia, https://en.wikipedia.org/wiki/Syringe, Obtained from the internet on Jun. 26, 2020.*
Choi et al (Inactivation of Ribonuclease and Other Enzymes by Peroxidizing Lipids and by Malonaldehyde. Biochemistry. 1969;8: 2827-2832).*
Brittain (Analytical Profiles of Drug Substances and Excipients. vol. 24 (1996), p. 434).*
Collagen (http://en.wikipedia.org/wiki/Collagen), Aug. 14, 2011.*
Peptide Bond (http://en.wikipedia. org/wiki/Peptide_bond), Aug. 14, 2011.*

(Continued)

*Primary Examiner* — Dwayne C. Jones
(74) *Attorney, Agent, or Firm* — Collen A. Beard; Advent, LLP

(57) ABSTRACT

Embolic compositions comprising macromers having a backbone comprising a polymeric backbone comprising units with a 1,2-diol or 1,3-diol structure, such as polyvinyl alcohol, and pendant chains bearing crosslinkable groups and, optionally, other modifiers. When crosslinked, the macromers form hydrogels having many properties advantageous for use as embolic agents to block and fill lumens and spaces. The embolic compositions can be used as liquid embolic agents and crosslinked in situ or as preformed embolic articles, such as microspheres.

12 Claims, No Drawings

(56) References Cited

U.S. PATENT DOCUMENTS

| | | | | |
|---|---|---|---|---|
| 5,932,674 | A | 8/1999 | Muller | |
| 5,942,209 | A | 8/1999 | Leavitt et al. | |
| 5,981,826 | A | 11/1999 | Ku et al. | |
| 6,028,164 | A | 2/2000 | Loomis | |
| 6,037,366 | A | 3/2000 | Krall et al. | |
| 6,060,534 | A | 5/2000 | Ronan | |
| 6,083,524 | A | 7/2000 | Sawhney et al. | |
| 6,129,761 | A | 10/2000 | Hubbell | |
| 6,153,211 | A | 11/2000 | Hubbell et al. | |
| 6,162,844 | A | 12/2000 | Lally et al. | 523/106 |
| 6,166,130 | A | 12/2000 | Rhee | |
| 6,191,193 | B1 | 2/2001 | Lee et al. | |
| 6,201,065 | B1 | 3/2001 | Pathak | |
| 6,265,509 | B1 * | 7/2001 | Muller | C08F 8/30 522/85 |
| 6,680,046 | B1 * | 1/2004 | Boschetti | A61P 35/00 424/9.1 |
| 6,818,018 | B1 * | 11/2004 | Sawhney | A61L 27/34 523/113 |
| RE47,121 | E * | 11/2018 | Goupil | C08F 261/04 |

FOREIGN PATENT DOCUMENTS

| | | |
|---|---|---|
| WO | WO 95/09659 | 4/1995 |
| WO | WO 97/04656 | 2/1997 |
| WO | WO 97/04657 | 2/1997 |
| WO | WO 97/04813 | 2/1997 |
| WO | WO 97/22371 | 6/1997 |
| WO | WO 97/22372 | 6/1997 |
| WO | WO 97/27888 | 8/1997 |
| WO | WO 98/04312 | 2/1998 |
| WO | WO 98/17200 | 4/1998 |
| WO | WO 98/17201 | 4/1998 |
| WO | WO 99/12577 | 3/1999 |
| WO | WO 99/44643 | 9/1999 |
| WO | WO 00/09087 | 2/2000 |
| WO | WO 00/09088 | 2/2000 |
| WO | WO 00/09190 | 2/2000 |
| WO | WO 00/09199 | 2/2000 |
| WO | WO 00/23054 | 4/2000 |
| WO | WO 00/35373 | 6/2000 |
| WO | WO 00/45868 | 8/2000 |
| WO | WO 00/50103 | 8/2000 |
| WO | WO 00/56370 | 9/2000 |
| WO | WO 00/56380 | 9/2000 |
| WO | WO 00/62827 | 10/2000 |
| WO | WO 00/64977 | 11/2000 |
| WO | WO 01/16210 | 3/2001 |
| WO | WO 01/17574 | 3/2001 |
| WO | WO 01/44307 | 6/2001 |
| WO | WO 01/55360 | 6/2001 |
| WO | WO 01/70132 | 9/2001 |
| WO | WO 01/70289 | 9/2001 |
| WO | WO 01/70290 | 9/2001 |
| WO | WO 01/70291 | 9/2001 |
| WO | WO 01/72281 | 10/2001 |
| WO | WO 02/16443 | 2/2002 |

OTHER PUBLICATIONS

Thanoo, B.C., Sunny, M.C. and Jayakrishan, A. Preparation and properties of barium sulphate and methyl iothalamate loaded PVA microspheres as radiopaque particulate emboli. 1991. Journal of Applied Biomateriais, 2: 67-72.

* cited by examiner

EMBOLIC COMPOSITIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*More than one reissue application has been filed for the reissue of U.S. Pat. No. 8,221,735. The reissue applications are application Ser. No. 16/045,954 (the present application) filed on Jul. 26, 2018; Ser. No. 14/334,294 (now U.S. Pat. No. RE47,121) filed on Jul. 17, 2014; and Ser. No. 14/659,377 (now U.S. Pat. No. RE47,873) filed on Mar. 16, 2015. Both Ser. Nos. 14/659,377 and 16/045,954 are continuation reissues of Ser. No. 14/344,294.*

RELATED APPLICATIONS

This application is a Divisional of U.S. Ser. No. 10/465,497, which was filed on Jun. 19, 2003, now abandoned which is a Divisional of U.S. Ser. No. 09/804,963, which was filed on Mar. 13, 2001, now U.S. pat. No. 6,676,971 and claims priority to U.S. Ser. No. 60/188,975 filed on Mar. 13, 2000 and U.S. Ser. No. 60/254,697 filed on Dec. 11, 2000.

BACKGROUND OF THE INVENTION

The invention relates to compositions for use in embolic agents. More specifically, the invention relates to compositions including crosslinkable macromonomers (referred to herein as macromers) that form hydrogels useful in embolization.

Embolic agents are useful for a variety of bioapplications, such as occluding blood vessels, occluding other body lumens such as fallopian tubes, filling aneurysm sacs, as arterial sealants, and as puncture sealants. Embolization of blood vessels is performed for a number of reasons, e.g. to reduce blood flow to and encourage atrophy of tumors, such as in the liver, to reduce blood flow and induce atrophy of uterine fibroids, for treatment of vascular malformations, such as arteriovenous malformations (AVMs) and arteriovenous fistulas (AVFs), to seal endoleaks into aneurysm sacs, to stop uncontrolled bleeding, or to slow bleeding prior to surgery.

Gynecologic embolotherapy may be conducted for a variety of purposes including the treatment of uterine fibroids, the treatment of postpartum and post cesarean bleeding, the treatment of post surgical vaginal bleeding, the prevention and/or treatment of hemorrhage from ectopic pregnancy, prophylactically prior to myomectomy and in obstetrical patients at high risk for bleeding, such as those patients with placenta previa, placenta accreta, uterine fibroids, and twin fetal death.

Abdominal aortic aneurysms (AAA) and thoracic aortic aneurysms (TAA) are relatively rare but often fatal conditions. Open surgery, primarily using clips or ligation techniques, has been the traditional means of treating AAAs and TAAs. Endovascular techniques, i.e. the placement of a stent graft at the site of the aneurysm, have become more popular. The currently available stent graft products, however, are not well matched to the unpredictable and singular anatomy presented by the aneurysm and its surrounding vasculature. Often, there are leaks into the excluded aneurysm sac, termed endoleaks, due to several reasons, including feeder vessels into the sac, spaces between the stent graft and the vessel wall, or holes in the stent graft wall. Such endoleaks can cause the pressure within the aneurysm sac to increase and cause the aneurysm to further expand and to rupture. Various embolic materials, including the devices and materials discussed above, have been placed in the aneurysm sac to induce thrombosis or otherwise to pack the aneurysm sac to seal the endoleak. Embolic materials are also used to occlude feeder vessels into the sac. WO 00/56380 to Micro Therapeutics, Inc. discloses the use of precipitating polymers and prepolymers such as cyanoacrylate to seal endoleaks.

Chemoembolotherapy as used herein refers to the combination of providing mechanical blockage and highly localized, in situ delivery of chemotherapeutic agents. In the treatment of solid tumors, the chemotherapeutic agent acts as an adjunct to the embolization. A known clinical practice is mixing of chemotherapeutic agents with embolic PVA particles for the delivery of the drugs at tumor sites. This type of regional therapy may localize treatment at the site of the tumor, and therefore the therapeutic dose may be smaller than the effective systemic dose, reducing potential side effects and damage to healthy tissue. However, since the chemotherapeutic drug is simply suspended with the beads there is little or no sustained release.

One type of embolic agent that is commonly used for occluding vessels is polyvinyl alcohol (PVA) particles. Such particles are nonspherical and are nonuniform in both size and shape. The particles are delivered via catheter in the vessel upstream of their desired placement site. Upon release, the particles are carried downstream whereupon they eventually lodge in the vessel. The problems associated with presently available PVA embolic particles include recanalization of the vessel, which may require follow up procedures, extensive mixing required to keep the particles suspended during injection, slow injection times and blocking of the catheter due to the high friction coefficient (due to the irregular shape and size of the particles), and inflammation. Other disadvantages of the use of the presently available PVA embolizing particles include lack of control as to where the particles eventually deposit, again due to the size irregularity. Some particles may continue downstream during administration and lodge in the vessel at a point past the desired site of embolization. Some particles may dislodge in the future and drift downstream.

Another issue with the presently available PVA embolic particles is that they are generally made using an aldehyde, such as gluteraldehyde. Such particles must be extracted prior to use, and may contain amounts of the aldehyde in the final product.

BioSphere Medical, Inc. markets microspheres for embolization made from acrylic polymer and impregnated with porcine gelatin. An obvious disadvantage of this product is that it may cause an immune reaction in patients who are sensitive to collagen or gelatin.

Other types of embolic materials that have been used include solid structures such as metallic microcoils, expandable balloons, and expandable materials such as temperature responsive preformed solid polymers and PVA sponges. Microcoils and balloons are limited to use in larger vessels and are prone to recanalization. Extrusion techniques have also been used to deliver extruded polymers to the intended site.

Liquid embolic agents have been developed, which can be delivered to the intended site via a catheter or a syringe, whereupon they solidify to form a solid plug or mass.

Temperature responsive polymers have been proposed as embolic agents, as described in WO 00/45868 to University of California. These polymers are in a liquid state when delivered to the intended site and harden in response to the increased temperature of the body.

Another type of liquid embolic agent is compositions containing a polymer in an organic solvent, wherein the polymer precipitates as the solvent is displaced by aqueous based body fluids. See, e.g., U.S. Pat. No. 6,051,607 to Greff and U.S. Pat. No. 5,925,683 to Park. A disadvantage of such products is that the polymer may remain in liquid form for a period of time while the solvent dissipates. The solvent may not completely dissipate from the center of the polymer mass, creating a mass with a solid shell and liquid center. The solvent concentration at the point of injection may increase to a point where small strings of unsolidified polymer material may separate from the polymer mass and be carried away in the blood stream where they can occlude an undesired vascular location. Moreover, the catheter used to deliver the polymer/solvent mixture is typically flushed with solvent before use. This must be done carefully to avoid vascular damage from the solvent.

Another type of liquid embolic agent is monomers that polymerize upon exposure to blood, such as cyanoacrylate. See, e.g. U.S. Pat. No. 6,037,366 to Krall et al. and WO 00/56370 to Micro Therapeutics, Inc. The conventional cyanoacrylate type embolic material is injected into the site of an aneurysm with difficulty because it quickly undergoes curing polymerization in the blood vessel. The material can be very adhesive and a catheter inserted into the blood vessel to deliver the material must be extracted at a stroke as soon as the injection of the material into the site of disease is completed to avoid the catheter being adhered in place. Thus, the material is not easy to handle. The injection cannot be repeated even when the occlusion is imperfect. This embolic material is further disadvantageous in that it can inflict a grave stimulus to the wall of the blood vessel and induce a strong inflammatory reaction.

WO 00/09190 to Incept LLC discloses embolic agents made from two or more liquid polymers that crosslink when combined. The components can be combined in situ at the intended site of embolization.

SUMMARY OF THE INVENTION

The invention relates to embolic compositions comprising macromers having a backbone of a polymer having units with a 1,2-diol and/or 1,3-diol structure. Such polymers include polyvinyl alcohol (PVA) and hydrolyzed copolymers of vinyl acetate, for example, copolymers with vinyl chloride, N-vinylpyrrolidone, etc. The backbone polymer contains pendant chains bearing crosslinkable groups and, optionally, other modifiers. When crosslinked, the macromers form hydrogels advantageous for use as embolic agents to block and fill lumens and spaces.

In one embodiment, the embolic compositions are preformed into embolic articles before introduction into the body. In another embodiment, the embolic compositions are used as liquid embolic agents and formed into a hydrogel in situ.

The embolic compositions can be used for a variety of applications such as, but not limited to, vascular occlusion for treatment of tumors or fibroids, occlusion of vascular malformations, such as arteriovenous malformations (AVM), occlusion of left atrial appendages, fillers for aneurysm sacs, endoleak sealants, arterial sealants, puncture sealants, and occlusion of other lumens such as fallopian tubes.

In one embodiment, the embolic composition forms a permanent occlusion or mass. In another embodiment, the embolic composition forms a temporary or reversible (the terms temporary and reversible are herein used interchangeably) occlusion or mass. Temporary occlusion may be desired, for example, in treatment of tumors, to allow for recanalization and reapplication of a chemotherapeutic agent to the tumor. As another example, temporary occlusion may be desirable when using the embolic composition for temporary sterilization. Temporary occlusion can be achieved by using a fully or partially degradable embolic composition or a composition that degrades in response to an applied condition, such as a change in temperature or pH. Occlusion can also be reversed using devices designed for recanalization.

The processes for using the embolic compositions as liquid embolic agents include delivering the macromers to the intended site of embolization, or upstream of the intended site, using a delivery device such as a catheter or syringe. The macromers are then crosslinked into a hydrogel, generally upon exposure to a crosslinking initiator. In one embodiment, the macromers are dissolved in a biocompatible solution prior to administration. In one embodiment, the macromers are exposed to the crosslinking initiator before they are administered to the intended site of embolization.

DETAILED DESCRIPTION OF THE INVENTION

The term "embolic" or "embolizing" refers to a composition or agent introduced into a space, a cavity, or the lumen of a blood vessel or other like passageway that partially or totally fills the space or cavity or partially or totally plugs the lumen. For example, an embolic composition can be used for occlusion of a vessel leading to a tumor or fibroid, occlusion of a vascular malformation, such as an arteriovenous malformation (AVM), occlusion of a left atrial appendage, as a filler for an aneurysm sac, as an endoleak sealant, as an arterial sealant, as a puncture sealant, or for occlusion of any other lumen such as, for example, a fallopian tube.

As used herein, the term "lumen" is intended to refer to various hollow organs or vessels of the body, such as veins, arteries, intestines, fallopian tubes, trachea, and the like.

The invention relates to embolic compositions comprising macromers having a backbone of a polymer having units with a 1,2-diol and/or 1,3-diol structure and having at least two pendant chains including a crosslinkable group and optionally pendant chains containing modifiers. The macromers form a hydrogel when crosslinked. In one embodiment, the embolic compositions are employed as liquid embolic agents, meaning that the composition is administered prior to complete crosslinking of the macromers. In another embodiment, the embolic compositions are employed as preformed crosslinked hydrogel articles. The embolic compositions can also be used as a combination of liquid and preformed compositions.

The embolic compositions can be produced very simply and efficiently due to a number of factors. Firstly, the starting materials, such as polyhydroxy polymer backbones, are inexpensive to obtain or prepare. Secondly, the macromers are stable, so that they can be subjected to very substantial purification. The crosslinking can therefore be carried out using a macromer that is highly pure, containing substantially no unpolymerized constituents. Furthermore, the crosslinking can be carried out in purely aqueous solutions. Aldehyde is not required.

I. The Embolic Compositions

The Macromer Backbone

The macromers have a backbone of a polymer comprising units having a 1,2-diol or 1,3-diol structure, such as polyhydroxy polymers. For example, polyvinyl alcohol (PVA) or copolymers of vinyl alcohol contain a 1,3-diol skeleton. The backbone can also contain hydroxyl groups in the form of 1,2-glycols, such as copolymer units of 1,2-dihydroxyethylene. These can be obtained, for example, by alkaline hydrolysis of vinyl acetate-vinylene carbonate copolymers. Other polymeric diols can be used, such as saccharides.

In addition, the macromers can also contain small proportions, for example, up to 20%, preferably up to 5%, of comonomer units of ethylene, propylene, acrylamide, methacrylamide, dimethacrylamide, hydroxyethyl methacrylate, alkyl methacrylates, alkyl methacrylates which are substituted by hydrophilic groups, such as hydroxyl, carboxyl or amino groups, methyl acrylate, ethyl acrylate, vinylpyrrolidone, hydroxyethyl acrylate, allyl alcohol, styrene, polyalkylene glycols, or similar comonomers usually used.

Polyvinyl alcohols that can be used as macromer backbones include commercially available PVAs, for example Vinol® 107 from Air Products (MW 22,000 to 31,000, 98 to 98.8% hydrolyzed), Polysciences 4397 (MW 25,000, 98.5% hydrolyzed), BF 14 from Chan Chun, Elvanol® 90-50 from DuPont and UF-120 from Unitika. Other producers are, for example, Nippon Gohsei (Gohsenol®), Monsanto (Gelvatol®), Wacker (Polyviol®), Kuraray, Deriki, and Shin-Etsu. In some cases it is advantageous to use Mowiol® products from Hoechst, in particular those of the 3-83, 4-88, 4-98, 6-88, 6-98, 8-88, 8-98, 10-98, 20-98, 26-88, and 40-88 types.

It is also possible to use copolymers of hydrolyzed or partially hydrolyzed vinyl acetate, which are obtainable, for example, as hydrolyzed ethylene-vinyl acetate (EVA), or vinyl chloride-vinyl acetate, N-vinylpyrrolidone-vinyl acetate, and maleic anhydride-vinyl acetate. If the macromer backbones are, for example, copolymers of vinyl acetate and vinylpyrrolidone, it is again possible to use commercially available copolymers, for example the commercial products available under the name Luviskol® from BASF. Particular examples are Luviskol VA 37 HM, Luviskol VA 37 E and Luviskol VA 28. If the macromer backbones are polyvinyl acetates, Mowilith 30 from Hoechst is particularly suitable.

Polyvinyl alcohols that can be derivatized as described herein preferably have a molecular weight of at least about 2,000. As an upper limit, the PVA may have a molecular weight of up to 1,000,000. Preferably, the PVA has a molecular weight of up to 300,000, especially up to approximately 130,000, and especially preferably up to approximately 60,000.

The PVA usually has a poly(2-hydroxy)ethylene structure. The PVA derivatized in accordance with the disclosure may, however, also comprise hydroxy groups in the form of 1,2-glycols.

The PVA system can be a fully hydrolyzed PVA, with all repeating groups being —$CH_2$—CH(OH), or a partially hydrolyzed PVA with varying proportions (1% to 25%) of pendant ester groups. PVA with pendant ester groups have repeating groups of the structure $CH_2$—CH(OR) where R is $COCH_3$ group or longer alkyls, as long as the water solubility of the PVA is preserved. The ester groups can also be substituted by acetaldehyde or butyraldehyde acetals that impart a certain degree of hydrophobicity and strength to the PVA. For an application that requires an oxidatively stable PVA, the commercially available PVA can be broken down by $NaIO_4$—$KMnO_4$ oxidation to yield a small molecular weight (2000 to 4000) PVA.

The PVA is prepared by basic or acidic, partial or virtually complete hydrolysis of polyvinyl acetate. In a preferred embodiment, the PVA comprises less than 50% of vinyl acetate units, especially less than about 25% of vinyl acetate units. Preferred amounts of residual acetate units in the PVA, based on the sum of vinyl alcohol units and acetate units, are approximately from 3 to 25%.

Crosslinkable Groups

The macromers have at least two pendant chains containing groups that can be crosslinked. The term group includes single polymerizable moieties, such as an acrylate, as well as larger crosslinkable regions, such as oligomeric or polymeric regions. The crosslinkers are desirably present in an amount of from approximately 0.01 to 10 milliequivalents of crosslinker per gram of backbone (meq/g), more desirably about 0.05 to 1.5 meq/g. The macromers can contain more than one type of crosslinkable group.

The pendant chains are attached via the hydroxyl groups of the polymer backbone. Desirably, the pendant chains having crosslinkable groups are attached via cyclic acetal linkages to the 1,2-diol or 1,3-diol hydroxyl groups.

Crosslinking of the macromers may be via any of a number of means, such as physical crosslinking or chemical crosslinking. Physical crosslinking includes, but is not limited to, complexation, hydrogen bonding, desolvation, Van der wals interactions, and ionic bonding. Chemical crosslinking can be accomplished by a number of means including, but not limited to, chain reaction (addition) polymerization, step reaction (condensation) polymerization and other methods of increasing the molecular weight of polymers/oligomers to very high molecular weights. Chain reaction polymerization includes, but is not limited to, free radical polymerization (thermal, photo, redox, atom transfer polymerization, etc.), cationic polymerization (including onium), anionic polymerization (including group transfer polymerization), certain types of coordination polymerization, certain types of ring opening and metathesis polymerizations, etc. Step reaction polymerizations include all polymerizations which follow step growth kinetics including but not limited to reactions of nucleophiles with electrophiles, certain types of coordination polymerization, certain types of ring opening and metathesis polymerizations, etc. Other methods of increasing molecular weight of polymers/oligomers include but are not limited to polyelectrolyte formation, grafting, ionic crosslinking, etc.

Various crosslinkable groups are known to those skilled in the art and can be used, according to what type of crosslinking is desired. For example, hydrogels can be formed by the ionic interaction of divalent cationic metal ions (such as $Ca^{+2}$ and $Mg^{+2}$) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. Multifunctional cationic polymers, such as poly(1-lysine), poly(allylamine), poly (ethyleneimine), poly(guanidine), poly(vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. Block and graft copolymers of water soluble and insoluble polymers exhibit such effects, for example, poly (oxyethylene)-poly(oxypropylene) block copolymers, copolymers of poly(oxyethylene) with poly(styrene), poly(caprolactone), poly(butadiene), etc.

Solutions of other synthetic polymers such as poly(N-alkylacrylamides) also form hydrogels that exhibit thermoreversible behavior and exhibit weak physical crosslinks on warming. A two component aqueous solution system may be selected so that the first component (among other components) consists of poly(acrylic acid) or poly(methacrylic acid) at an elevated pH of around 8-9 and the other component consists of (among other components) a solution of poly (ethylene glycol) at an acidic pH, such that the two solutions on being combined in situ result in an immediate increase in viscosity due to physical crosslinking.

Other means for polymerization of the macromers also may be advantageously used with macromers that contain groups that demonstrate activity towards functional groups such as amines, imines, thiols, carboxyls, isocyanates, urethanes, amides, thiocyanates, hydroxyls, etc., which may be naturally present in, on, or around tissue. Alternatively, such functional groups optionally may be provided in some of the macromers of the composition. In this case, no external initiators of polymerization are needed and polymerization proceeds spontaneously when two complementary reactive functional groups containing moieties interact at the application site.

Desirable crosslinkable groups include (meth)acrylamide, (meth)acrylate, styryl, vinyl ester, vinyl ketone, vinyl ethers, etc. Particularly desirable are ethylenically unsaturated functional groups.

Ethylenically unsaturated groups can be crosslinked via free radical initiated polymerization, including via photoinitiation, redox initiation, and thermal initiation. Systems employing these means of initiation are well known to those skilled in the art. In one embodiment, a two part redox system is employed. One part of the system contains a reducing agent such as a ferrous salt. Various ferrous salts can be used, such as, for example, ferrous gluconate dihydrate, ferrous lactate dihydrate, or ferrous acetate. The other half of the solution contains an oxidizing agent such as hydrogen peroxide. Either or both of the redox solutions can contain macromer, or it may be in a third solution. The two solutions are combined to initiate the crosslinking.

Other reducing agents can be used, such as, but not limited to, cuprous salts, cerous salts, cobaltous salts, permanganate, and manganous salts. Ascorbate, for example, can be used as a coreductant to recycle the reductant and reduce the amount needed. This can reduce the toxicity of a ferrous based system. Other oxidizing agents that can be used include, but are not limited to, t-butyl hydroperoxide, t-butyl peroxide, benzoyl peroxide, cumyl peroxide, etc.

Specific Macromers

Specific macromers that are suitable for use in the embolic compositions are disclosed in U.S. Pat. Nos. 5,508,317, 5,665,840, 5,807,927, 5,849,841, 5,932,674, 5,939,489, and 6,011,077.

In one embodiment, units containing a crosslinkable group conform, in particular, to the formula I

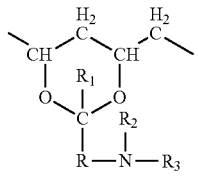

in which R is a linear or branched $C_1$-$C_8$ alkylene or a linear or branched $C_1$-$C_{12}$ alkane. Suitable alkylene examples include octylene, hexylene, pentylene, butylene, propylene, ethylene, methylene, 2-propylene, 2-butylene and 3-pentylene. Preferably lower alkylene R has up to 6 and especially preferably up to 4 carbon atoms. The groups ethylene and butylene are especially preferred. Alkanes include, in particular, methane, ethane, n- or isopropane, n-, sec- or tert-butane, n- or isopentane, hexane, heptane, or octane. Preferred groups contain one to four carbon atoms, in particular one carbon atom.

$R_1$ is hydrogen, a $C_1$-$C_6$ alkyl, or a cycloalkyl, for example, methyl, ethyl, propyl or butyl and $R_2$ is hydrogen or a $C_1$-$C_6$ alkyl, for example, methyl, ethyl, propyl or butyl. $R_1$ and $R_2$ are preferably each hydrogen.

$R_3$ is an olefinically unsaturated electron attracting copolymerizable radical having up to 25 carbon atoms. In one embodiment, $R_3$ has the structure

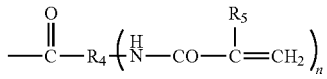

where $R_4$ is the

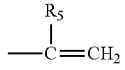

group if n=zero, or the

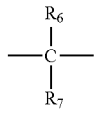

bridge if n=1;

$R_5$ is hydrogen or $C_1$-$C_4$ alkyl, for example, n-butyl, n- or isopropyl, ethyl, or methyl;

n is zero or 1, preferably zero; and $R_6$ and $R_7$, independently of one another, are hydrogen, a linear or branched $C_1$-$C_8$ alkyl, aryl or cyclohexyl, for example one of the following: octyl, hexyl, pentyl, butyl, propyl, ethyl, methyl, 2-propyl, 2-butyl or 3-pentyl. $R_6$ is preferably hydrogen or the $CH_3$ group, and $R_7$ is preferably a $C_1$-$C_4$ alkyl group. $R_6$ and $R_7$ as aryl are preferably phenyl.

In another embodiment, $R_3$ is an olefinically unsaturated acyl group of formula $R_8$—CO—, in which $R_8$ is an olefinically unsaturated copolymerizable group having from 2 to 24 carbon atoms, preferably from 2 to 8 carbon atoms, especially preferably from 2 to 4 carbon atoms. The olefinically unsaturated copolymerizable radical $R_8$ having from 2 to 24 carbon atoms is preferably alkenyl having from 2 to 24 carbon atoms, especially alkenyl having from 2 to 8 carbon atoms and especially preferably alkenyl having from 2 to 4 carbon atoms, for example ethenyl, 2-propenyl, 3-propenyl, 2-butenyl, hexenyl, octenyl or dodecenyl. The groups ethenyl and 2-propenyl are preferred, so that the group —CO—$R_8$ is the acyl radical of acrylic or methacrylic acid.

In another embodiment, the group $R_3$ is a radical of formula $$—[CO—NH—(R_9—NH—CO—O)_q—R_{10}—O]_p—CO—R_8$$

wherein p and q are zero or one and $R_9$ and $R_{10}$ are each independently lower alkylene having from 2 to 8 carbon atoms, arylene having from 6 to 12 carbon atoms, a saturated divalent cycloaliphatic group having from 6 to 10 carbon atoms, arylenealkylene or alkylenearylene having from 7 to 14 carbon atoms or arylenealkylenearylene having from 13 to 16 carbon atoms, and $R_8$ is as defined above.

Lower alkylene $R_9$ or $R_{10}$ preferably has from 2 to 6 carbon atoms and is especially straight-chained. Suitable examples include propylene, butylene, hexylene, dimethylethylene and, especially preferably, ethylene.

Arylene $R_9$ or $R_{10}$ is preferably phenylene that is unsubstituted or is substituted by lower alkyl or lower alkoxy, especially 1,3-phenylene or 1,4-phenylene or methyl-1,4-phenylene.

A saturated divalent cycloaliphatic group $R_9$ or $R_{10}$ is preferably cyclohexylene or cyclohexylene-lower alkylene, for example cyclohexylenemethylene, that is unsubstituted or is substituted by one or more methyl groups, such as, for example, trimethylcyclohexylenemethylene, for example the divalent isophorone radical.

The arylene unit of alkylenearylene or arylenealkylene $R_9$ or $R_{10}$ is preferably phenylene, unsubstituted or substituted by lower alkyl or lower alkoxy, and the alkylene unit thereof is preferably lower alkylene, such as methylene or ethylene, especially methylene. Such radicals $R_9$ or $R_{10}$ are therefore preferably phenylenemethylene or methylenephenylene.

Arylenealkylenearylene $R_9$ or $R_{10}$ is preferably phenylene-lower alkylene-phenylene having up to 4 carbon atoms in the alkylene unit, for example phenyleneethylenephenylene.

The groups $R_9$ and $R_{10}$ are each independently preferably lower alkylene having from 2 to 6 carbon atoms, phenylene, unsubstituted or substituted by lower alkyl, cyclohexylene or cyclohexylene-lower alkylene, unsubstituted or substituted by lower alkyl, phenylene-lower alkylene, lower alkylenephenylene or phenylene-lower alkylene-phenylene.

The group —$R_9$—NH—CO—O— is present when q is one and absent when q is zero. Macromers in which q is zero are preferred.

The group —CO—NH—$(R_9—NH—CO—O)_q—R_{10}$—O— is present when p is one and absent when p is zero. Macromers in which p is zero are preferred.

In macromers in which p is one, q is preferably zero. Macromers in which p is one, q is zero, and $R_{10}$ is lower alkylene are especially preferred.

All of the above groups can be monosubstituted or polysubstituted, examples of suitable substituents being the following: $C_1$-$C_4$ alkyl, such as methyl, ethyl or propyl, —COOH, —OH, —SH, $C_1$-$C_4$ alkoxy (such as methoxy, ethoxy, propoxy, butoxy, or isobutoxy), —$NO_2$, —$NH_2$, —NH($C_1$-$C_4$), —NH—CO—$NH_2$, —N($C_1$-$C_4$ alkyl)$_2$, phenyl (unsubstituted or substituted by, for example, —OH or halogen, such as Cl, Br or especially I), —S($C_1$-$C_4$ alkyl), a 5- or 6-membered heterocyclic ring, such as, in particular, indole or imidazole, —NH—C(NH)—$NH_2$, phenoxyphenyl (unsubstituted or substituted by, for example, —OH or halogen, such as Cl, Br or especially I), an olefinic group, such as ethylene or vinyl, and CO—NH—C(NH)—$NH_2$.

Preferred substituents are lower alkyl, which here, as elsewhere in this description, is preferably $C_1$-$C_4$ alkyl, $C_1$-$C_4$ alkoxy, COOH, SH, —$NH_2$, —NH($C_1$-$C_4$ alkyl), —N($C_1$-$C_4$ alkyl)$_2$ or halogen. Particular preference is given to $C_1$-$C_4$ alkyl, $C_1$-$C_4$ alkoxy, COOH and SH.

For the purposes of this invention, cycloalkyl is, in particular, cycloalkyl, and aryl is, in particular, phenyl, unsubstituted or substituted as described above.

Modifiers

The macromers can include further modifier groups and crosslinkable groups. Some such groups are described in U.S. Pat. Nos. 5,508,317, 5,665,840, 5,807,927, 5,849,841, 5,932,674, 5,939,489, and 6,011,077. Crosslinkable groups and the optional further modifier groups can be bonded to the macromer backbone in various ways, for example through a certain percentage of the 1,3-diol units being modified to give a 1,3-dioxane, which contains a crosslinkable group, or a further modifier, in the 2-position. Modifiers that might be attached to the backbone include those to modify the hydrophobicity, active agents or groups to allow attachment of active agents, photoinitiators, modifiers to enhance or reduce adhesiveness, modifiers to impart thermoresponsiveness, modifiers to impart other types of responsiveness, and additional crosslinking groups. These modifiers may be attached to the hydroxyl groups in the backbone, or to other monomeric units included in the backbone.

Attaching a cellular adhesion promoter to the macromers can enhance cellular attachment or adhesiveness of the embolic agents formed by the embolic compositions. These agents are well known to those skilled in the art and include carboxymethyl dextran, proteoglycans, collagen, gelatin, glucosaminoglycans, fibronectin, lectins, polycations, and natural or synthetic biological cell adhesion agents such as RGD peptides.

Having pendant ester groups that are substituted by acetaldehyde or butyraldehyde acetals, for example, can increase the hydrophobicity of the macromers and the formed hydrogel. Hydrophobic groups can desirably be present in an amount from about 0 to 25%.

It may also be desirable to include on the macromer a molecule that allows visualization of the formed hydrogel. Examples include dyes and molecules visualizable by magnetic resonance imaging.

Degradable Regions

The macromers can form a hydrogel that is degradable. Suitable degradable systems are described in U.S. patent application Ser. No. 09/714,700, titled "Degradable Poly (Vinyl Alcohol) Hydrogels" and filed on Nov. 15, 2000. In the degradable systems described in that application, the macromers include a degradable region in the backbone or on a pendant chain. The degradable region is preferably degradable under in vivo conditions by hydrolysis. The degradable region can be enzymatically degradable. For example, the degradable region may be polymers and oligomers of glycolide, lactide, ε-caprolactone, other hydroxy acids, and other biologically degradable polymers that yield materials that are non-toxic or present as normal metabolites in the body. Preferred poly(α-hydroxy acids) are poly(glycolic acid), poly (DL-lactic acid) and poly(L-lactic acid). Other useful materials include poly(amino acids), poly(anhydrides), poly (orthoesters), poly(phosphazines), and poly (phosphoesters). Polylactones such as poly(ε-caprolactone), poly(ε-caprolactone), poly(δ-valerolactone) and poly(γ-butyrolactone), for example, are also useful. Enzymatically degradable linkages include poly(amino acids), gelatin, chitosan, and carbohydrates. The biodegradable regions may have a degree of polymerization ranging from one up to values that would yield a product that was not substantially water soluble. Thus, monomeric, dimeric, trimeric, oligomeric, and polymeric regions may be used. The biodegradable region could, for example, be a single methacrylate group.

Biodegradable regions can be constructed from polymers or monomers using linkages susceptible to biodegradation, such as ester, acetal, carbonate, peptide, anhydride, orthoester, phosphazine, and phosphoester bonds. The biodegradable regions may be arranged within the macromers such that the formed hydrogel has a range of degradability, both in terms of extent of degradation, whether complete or partial, and in terms of time to complete or partial degradation.

Synthesis of Macromers

The macromers can be made by general synthetic methods known to those skilled in the art. The specific macromers discussed above can be made as described in U.S. Pat. Nos. 5,508,317, 5,665,840, 5,807,927, 5,849,841, 5,932,674, 5,939,489, and 6,011,077.

The specific macromers described above are extraordinarily stable. Spontaneous crosslinking by homopolymerization does not typically occur. The macromers can furthermore be purified in a manner known per se, for example by precipitation with organic solvents, such as acetone, extraction in a suitable solvent, washing, dialysis, filtration, or ultrafiltration. Ultrafiltration is especially preferred. By means of the purification process the macromers can be obtained in extremely pure form, for example in the form of concentrated aqueous solutions that are free, or at least substantially free, from reaction products, such as salts, and from starting materials.

The preferred purification process for the macromers of the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the sodium chloride content of the solution, which can be determined simply in a known manner, such as by conductivity measurements.

The macromers are crosslinkable in an extremely effective and controlled manner.

Vinylic Comonomers

The process for polymerization of the macromers may comprise, for example, crosslinking a macromer comprising units of formula I, especially in substantially pure form, that is to say, for example, after single or repeated ultrafiltration, preferably in solution, especially in aqueous solution, in the absence or presence of an additional vinylic comonomer.

The vinylic comonomer may be hydrophilic or hydrophobic, or a mixture of a hydrophobic and a hydrophilic vinylic monomer. Generally, approximately from 0.01 to 80 units of a typical vinylic comonomer react per unit of formula I, especially from 1 to 30 units per unit of formula I, and especially preferably from 5 to 20 units per unit of formula I.

It is also preferable to use a hydrophobic vinylic comonomer or a mixture of a hydrophobic vinylic comonomer with a hydrophilic vinylic comonomer, the mixture comprising at least 50 percent by weight of a hydrophobic vinylic comonomer. In that manner the mechanical properties of the polymer can be improved without the water content falling substantially. In principle, however, both conventional hydrophobic vinylic comonomers and conventional hydrophilic vinylic comonomers are suitable for copolymerization with the macromer.

Suitable hydrophobic vinylic comonomers include, without the list being exhaustive, $C_1$-$C_{18}$ alkyl acrylates and methacrylates, $C_3$-$C_{18}$ alkyl acrylamides and methacrylamides, acrylonitrile, methacrylonitrile, vinyl-$C_1$-$C_{18}$ alkanoates, $C_2$-$C_{18}$ alkenes, $C_2$-$C_{18}$ haloalkenes, styrene, $C_1$-$C_6$ alkylstyrene, vinyl alkyl ethers, in which the alkyl moiety contains from 1 to 6 carbon atoms, $C_2$-$C_{10}$ perfluoroalkyl acrylates and methacrylates or correspondingly partially fluorinated acrylates and methacrylates, $C_3$-$C_{12}$ perfluoroalkyl-ethylthiocarbonylaminoethyl acrylates and methacrylates, acryloxy- and methacryloxy-alkylsiloxanes, N-vinylcarbazole, $C_3$-$C_{12}$ alkyl-esters of maleic acid, fumaric acid, itaconic acid, mesaconic acid and the like. $C_1$-$C_4$ alkyl esters of vinylically unsaturated carboxylic acids having from 3 to 5 carbon atoms or vinyl esters of carboxylic acids having up to 5 carbon atoms, for example, are preferred.

Examples of suitable hydrophobic vinylic comonomers include methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropylpentamethyldisiloxane and bis(methacryloxypropyl) tetramethyldisiloxane.

Suitable hydrophilic vinylic comonomers include, without the list being exhaustive, hydroxy-substituted lower alkyl acrylates and methacrylates, acrylamide, methacrylamide, lower alkyl acrylamides and methacrylamides, ethoxylated acrylates and methacrylates, hydroxy-substituted lower alkyl acrylamides and methacrylamides, hydroxy-substituted lower alkyl vinyl ethers, sodium ethylenesulfonate, sodium styrenesulfonate, 2-acrylamido-2-methylpropanesulfonic acid (AMPS® monomer from Lubrizol Corporation), N-vinylpyrrole, N-vinylsuccinimide, N-vinylpyrrolidone, 2- or 4-vinylpyridine, acrylic acid, methacrylic acid, amino- (the term "amino" also including quaternary ammonium), mono-lower alkylamino- or di-lower alkylamino-lower alkyl acrylates and methacrylates, allyl alcohol and the like. Hydroxy-substituted $C_2$-$C_4$ alkyl (meth)acrylates, five- to seven-membered N-vinyl lactams, N,N-di-$C_1$-$C_4$ alkyl(meth)acrylamides and vinylically unsaturated carboxylic acids having a total of from 3 to 5 carbon atoms, for example, are preferred.

Contrast Agents

It may be desirable to include a contrast agent in the embolic compositions. A contrast agent is a biocompatible (non-toxic) material capable of being monitored by, for example, radiography. The contrast agent can be water soluble or water insoluble. Examples of water soluble contrast agents include metrizamide, iopamidol, iothalamate sodium, iodomide sodium, and meglumine. Iodinated liquid contrast agents include Omnipaque®, Visipaque®, and Hypaque-76®. Examples of water insoluble contrast agents are tantalum, tantalum oxide, barium sulfate, gold, tungsten, and platinum. These are commonly available as particles preferably having a size of about 10 μm or less.

The contrast agent can be added to the embolic compositions prior to administration. Both solid and liquid contrast agents can be simply mixed with a solution of the liquid embolic compositions or with the solid articles. Liquid contrast agent can be mixed at a concentration of about 10 to 80 volume percent, more desirably about 20 to 50 volume percent. Solid contrast agents are desirably added in an amount of about 10 to 40 weight percent, more preferably about 20 to 40 weight percent.

Occlusive Devices

It may be desirable to use the embolic compositions in combination with one or more occlusive devices. Such devices include balloons, microcoils, and other devices known to those skilled in the art. The device can be placed at the site to be occluded or filled before, during, or after the embolic composition is administered. For example, an occlusive coil can be placed in an aneurysm sac to be filled and the liquid embolic composition can be injected into the sac to fill the space around the coil. An advantage of using an occlusive device along with the embolic composition is that it may provide greater rigidity to the filling.

Active Agents

An effective amount of one or more biologically active agents can be included in the embolic compositions. It may be desirable to deliver the active agent from the formed hydrogel. Biologically active agents that it may be desirable to deliver include prophylactic, therapeutic, and diagnostic agents including organic and inorganic molecules and cells (collectively referred to herein as an "active agent" or "drug"). A wide variety of active agents can be incorporated into the hydrogel. Release of the incorporated additive from the hydrogel is achieved by diffusion of the agent from the hydrogel, degradation of the hydrogel, and/or degradation of a chemical link coupling the agent to the polymer. In this context, an "effective amount" refers to the amount of active agent required to obtain the desired effect.

Examples of active agents that can be incorporated include, but are not limited to, anti-angiogenic agents, chemotherapeutic agents, radiation delivery devices, such as radioactive seeds for brachytherapy, and gene therapy compositions.

Chemotherapeutic agents that can be incorporated include water soluble chemotherapeutic agents, such as cisplatin (platinol), doxorubicin (adriamycin, rubex), or mitomycin C (mutamycin). Other chemotherapeutic agents include iodinated fatty acid ethyl esters of poppy seed oil, such as lipiodol.

Cells can be incorporated into the embolic compositions, including cells to encourage tissue growth or cells to secrete a desired active agent. For example, cells that can be incorporated include fibroblasts, endothelial cells, muscle cells, stem cells, etc. Cells can be modified to secrete active agents such as growth factors.

Active agents can be incorporated into the liquid embolic compositions simply by mixing the agent with the embolic composition prior to administration. The active agent will then be entrapped in the hydrogel that is formed upon administration of the embolic composition. Active agents can be incorporated into the preformed embolic articles through encapsulation and other methods known in the art and discussed further below. The active agent can be in compound form or can be in the form of degradable or nondegradable nano or microspheres. It some cases, it may be possible and desirable to attach the active agent to the macromer or to the preformed article. The active agent may also be coated onto the surface of the preformed article. The active agent may be released from the macromer or hydrogel over time or in response to an environmental condition.

Other Additives

It may be desirable to include a peroxide stabilizer in redox initiated systems. Examples of peroxide stabilizers are Dequest® products from Solutia Inc., such as for example Dequest® 2010 and Dequest® 2060S. These are phosphonates and chelants that offer stabilization of peroxide systems. Dequest® 2060S is diethylenetriamine penta(methylene phosphonic acid). These can be added in amounts as recommended by the manufacturer.

It may be desirable to include fillers in the embolic compositions, such as fillers that leach out of the formed hydrogel over a period of time and cause the hydrogel to become porous. Such may be desirable, for example, where the embolic composition is used for chemoembolization and it may be desirable to administer a follow up dose of chemoactive agent. Appropriate fillers include calcium salts, for example.

Characteristics that can be Modified

The embolic compositions are highly versatile. A number of characteristics can be easily modified, making the embolic compositions suitable for a number of applications. For example, as discussed above, the polymer backbones can include comonomers to add desired properties, such as, for example, thermoresponsiveness, degradability, gelation speed, and hydrophobicity. Modifiers can be attached to the polymer backbone (or to pendant groups) to add desired properties, such as, for example, thermoresponsiveness, degradability, hydrophobicity, and adhesiveness. Active agents can also be attached to the polymer backbone using the free hydroxyl groups, or can be attached to pendant groups.

The gelation time of the liquid embolic compositions can be varied from about 0.5 seconds to as long as 10 minutes, and longer if desired. However, the preferred gelation time for most liquid embolic applications will be less than about 5 seconds, desirably less than about 2 seconds. The desired gelation time will depend upon whether it is desired to form a plug near the catheter tip or to form a more diffuse network. A longer gelation time will generally be required if crosslinking is initiated a distance from the intended embolic site.

The gelation time will generally be affected by, and can be modified by changing at least the following variables: the initiator system, crosslinker density, macromer molecular weight, macromer concentration (solids content), and type of crosslinker. A higher crosslinker density will provide faster gelation time; a lower molecular weight will provide a slower gelation time. A higher solids content will provide faster gelation time. For redox systems the gelation time can be designed by varying the concentrations of the redox components. Higher reductant and higher oxidant will provide faster gelation, higher buffer concentration and lower pH will provide faster gelation.

The firmness of the formed hydrogel will be determined in part by the hydrophilic/hydrophobic balance, where a higher hydrophobic percent provides a firmer hydrogel. The firmness will also be determined by the crosslinker density (higher density provides a firmer hydrogel), the macromer molecular weight (lower MW provides a firmer hydrogel), and the length of the crosslinker (a shorter crosslinker provides a firmer hydrogel).

The swelling of the hydrogel is inversely proportional to the crosslinker density. Generally, no or minimal swelling is desired, desirably less than about 10 percent.

Elasticity of the formed hydrogel can be increased by increasing the size of the backbone between crosslinks and decreasing the crosslinker density. Incomplete crosslinking will also provide a more elastic hydrogel. Preferably the elasticity of the hydrogel substantially matches the elasticity of the tissue to which the embolic composition is to administered.

Making Preformed Embolic Articles

Preformed articles are made, in general, by dissolving macromers in an appropriate solvent, shaping the macromers such as by pouring the macromer solution in a mold, if desired, and crosslinking the macromers. A mold is suitable for use in making rod shaped articles, for example. Microparticles can be made by forming a hydrogel sheet and milling it into particles. Such particles will be irregular in size and shape.

In one embodiment, the preformed articles are spherical microparticles termed microspheres. Microparticles can be made by a number of techniques known to those skilled in the art, such as single and double emulsion, suspension polymerization, solvent evaporation, spray drying, and solvent extraction. Methods for making microspheres are described in the literature, for example, in Mathiowitz and Langer, J. Controlled Release 5:13-22 (1987); Mathiowitz et al., Reactive Polymers 6:275-283 (1987); Mathiowitz et al., J. Appl. Polymer Sci. 35:755-774 (1988); Mathiowitz et al., Scanning Microscopy 4:329-340 (1990); Mathiowitz et al., J. Appl. Polymer Sci., 45:125-134 (1992); and Benita et al., J. Pharm. Sci. 73:1721-1724 (1984).

In solvent evaporation, described for example in Mathiowitz et al., (1990), Benita et al. (1984), and U.S. Pat. No. 4,272,398, the macromers are dissolved in a solvent. If desired, an agent to be incorporated, either in soluble form or dispersed as fine particles, is added to the macromer solution, and the mixture is suspended in an aqueous phase that contains a surface active agent. The resulting emulsion is stirred until most of the solvent evaporates, leaving solid microspheres, which may be washed with water and dried overnight in a lyophilizer. The microspheres are polymerized, for example, by exposure to light.

In solvent removal, the macromers are dissolved in a solvent. The mixture can then be suspended in oil, such as silicon oil, by stirring, to form an emulsion. As the solvent diffuses into the oil phase, the emulsion droplets harden into solid polymer microspheres. The microspheres can be polymerized by exposure to light, for example.

Spray drying is implemented by passing the polymerizable macromers used to form the hydrogel through a nozzle, spinning disk or equivalent device to atomize the mixture to form fine droplets. The polymerizable macromers may be provided in a solution or suspension, such as an aqueous solution. The fine droplets are exposed to light, for example, to cause polymerization of the macromer and formation of the hydrogel microspheres.

In another embodiment, hydrogel particles are prepared by a water-in-oil emulsion or suspension process, wherein the polymerizable macromers and the substance to be incorporated, if desired, are suspended in a water-in-oil suspension and exposed to light to polymerize the macromers to form hydrogel particles incorporating the substance, such as a biologically active agent.

In another embodiment, microspheres can be formed by atomizing macromer solution into oil, followed by polymerization.

There are many variables that affect the size, size distribution, and quality of the micro spheres formed. An important variable is the choice of stabilizer. Good stabilizers have an HLB number from 1 to 4 and have some solubility in the oil phase. Some appropriate stabilizers include cellulose acetate butyrate (with 17% butyrate), sorbitan oleates, and dioctylsulphosuccinate. The amount and type of stabilizer will control the particle size and reduce coalescing of the particles during crosslinking. The oil can be a water-insoluble oil such as liquid paraffin, but water-insoluble halogenated solvents such as dichloroethane are commonly used. The ratio of water to oil is also important and desirably ranges from about 1:1 to 1:4.

Microspheres can be made in sizes ranging from about 10 microns to 2000 microns. In most applications it will be desirable to have a small size range of microspheres. The process used to make the microspheres can be controlled to achieve a particular desired size range of microspheres. Other methods, such as sieving, can be used to even more tightly control the size range of the microspheres.

Active agents can be included in the microspheres as described above. It may be desirable to coat the microspheres in modifiers or active agents, such as, for example, agents to increase cellular attachment. Such coating can be done by methods known to those skilled in the art.

II. Methods of Using the Embolic Compositions

The embolic compositions can be used for a variety of applications such as, but not limited to, vascular occlusion for treatment of tumors or fibroids, occlusion of vascular malformations, such as arteriovenous malformations (AVM), occlusion of the left atrial appendage, fillers for aneurysm sacs, endoleak sealants, arterial sealants, puncture sealants, and occlusion of other lumens such as fallopian tubes.

According to the general method, an effective amount of the embolic composition in an aqueous solvent is administered into a lumen or void. In one embodiment, the macromers are crosslinked in situ. The term "effective amount", as used herein, means the quantity of embolic composition needed to fill or block the biological structure of interest. The effective amount of embolic composition administered to a particular patient will vary depending upon a number of factors, including the sex, weight, age, and general health of the patient, the type, concentration, and consistency of the macromers and the hydrogel that results from crosslinking, and the particular site and condition being treated. The macromers may be administered over a number of treatment sessions.

The methods of using the liquid embolic compositions involve combining the components, including any comonomers and other additives, under conditions suitable for crosslinking of the macromers. The crosslinking is suitably carried out in a solvent. A suitable solvent is in principle any solvent that dissolves the macromers, for example water, alcohols, such as lower alkanols, for example ethanol or methanol, also carboxylic acid amides, such as dimethylformamide, or dimethyl sulfoxide, and also a mixture of suitable solvents, such as, for example, a mixture of water with an alcohol, such as, for example, a water/ethanol or a water/methanol mixture. The combination of the macromers is preferably carried out in a substantially aqueous solution. In accordance with the invention, the criterion that the macromer is soluble in water denotes in particular that the macromer is soluble in a concentration of approximately from 3 to 90 percent by weight, preferably approximately from 5 to 60 percent by weight, in a substantially aqueous solution. Insofar as it is possible in an individual case, macromer concentrations of more than 90 percent are also included in accordance with the invention.

Within the scope of this invention, substantially aqueous solutions of the macromer comprise especially solutions of the macromer in water, in aqueous salt solutions, especially in aqueous solutions that have an osmolarity of approximately from 200 to 450 milliosmol per 1000 ml (mOsm/l), preferably an osmolarity of approximately from 250 to 350 mOsm/l, especially approximately 300 mOsm/l, or in mixtures of water or aqueous salt solutions with physiologically tolerable polar organic solvents, such as, for example, glycerol. Solutions of the macromer in water or in aqueous salt solutions are preferred.

The viscosity of the solution of the macromer in the substantially aqueous solution is, within wide limits, not critical, but the solution should preferably be a flowable solution that can be delivered through an appropriately sized catheter or syringe. For delivery through microcatheters, viscosities in the range of about 10 to 50 cp are desirable. The viscosity can be substantially higher for delivery through a syringe. The viscosity will generally be controlled by the molecular weight of the macromers, the solids content of the solution, and the type and amount of contrast agent present.

The solids content of the solution will preferably range from about 2 percent by weight to about 30 percent by weight, desirably from about 6 to 12 percent by weight.

In one embodiment, the macromers are crosslinkable via free radical polymerization. In one embodiment, the crosslinking initiator is mixed with the macromer solution before administration, during administration, or after administration. For example, a redox system can be mixed with the macromer solution at the time of administration. In one embodiment, the crosslinking initiator may be present at the site of administration. For example, the initiator could be a substance, such as charged blood components, present at the site. Macromers can be used that crosslink when they contact each other. These can be mixed before, during, or after administration. In one embodiment, the crosslinking initiator is an applied stimulus, such as light or heat, which causes crosslinking. Suitable initiators are known for thermal, photo, and redox initiated polymerization. In a redox initiated system employing ferrous ion, peroxide, and ascorbate, the desired amounts of the components will be determined by concerns related to gelation speed, toxicity, extent of gelation desired, and stability. Very generally, the concentration of iron will be about 20 to 1000 ppm; the concentration of hydrogen peroxide will be about 10 to 1000 ppm; the pH will be about 3 to 7; the buffer concentration will be about 10 to 200 mM; and ascorbate concentration will be about 10 to 40 mM.

It may be desirable, if initiator is added before administration, to use a system that provides delayed crosslinking so that the embolic composition does not gel too early. Moreover, using delayed curing, the composition can assume or be formed into a desired shape before complete curing has occurred.

In some embodiments, the embolic composition should be injected before substantial crosslinking of the macromers has occurred. This allows the macromers to continue crosslinking in situ and prevents blockage of the syringe needle or catheter with gelled polymer. In addition, such in situ crosslinking may allow anchoring of the hydrogel to host tissue by covalently bonding with collagen molecules present within the host tissue.

Since the embolic compositions preferably comprise no undesired low-molecular-weight constituents, the crosslinked hydrogel products also comprise no such constituents. The embolic agents obtainable by the embolic compositions are therefore distinguished, in an advantageous embodiment, by the fact that they are extremely clean.

The embolic compositions can be used in combination with other methods. For example, the embolic compositions can be used with thermal or laser ablation, where the liquid embolic agent may be placed initially, followed by thermal or laser ablation, to provide a synergistic effect with enhanced efficacy.

The preformed embolic articles can be administered similarly to how solid embolic agents are presently administered. The microspheres will desirably be supplied in physiological, sterile saline. A microcatheter, for example, can be used to deliver the microspheres to the desired administration site. It may be desirable to mix a contrast agent and/or chemotherapeutic agent with the microspheres before administration.

Delivery Devices

The compositions can be delivered to the intended site of embolism using delivery devices generally known to those skilled in the art. In most cases, a catheter or syringe is used. In many cases, a multi-lumen catheter is used to deliver the liquid embolic composition to the intended site of administration. Generally, a two or three lumen catheter will be used, wherein the components of the composition which crosslink or initiate crosslinking are maintained in separate lumens until the time of administration. For example, in the case of a macromer that crosslinks via redox initiated free radical polymerization, one solution containing the reducing agent is delivered through a first lumen while a solution containing the oxidizing agent is delivered through a second lumen. The macromer can be in one or both of the solutions. A third lumen can be used to deliver contrast agent or the contrast agent can be in either or both of the redox solutions. A guidewire can be inserted through any of the lumens, and removed prior to delivery of a solution through that lumen.

In one embodiment, the catheter includes a mixing chamber at its delivery tip. A side by side "double D" lumen can be used, wherein the interior wall has been removed at the distal end to form an area where the two solutions combine before they are injected into the lumen or void. Alternatively, a coaxial catheter can be used, where one of the inner or outer lumens extends further than the other. Other types of multilumen catheters are disclosed in the art.

Vascular Embolics

The embolic compositions can be used to form a plug in a variety of biological lumens. For example, the compositions can be delivered endovascularly to plug the feeder vessel(s) of a tumor or a uterine fibroid. It may be desirable in some cases to use a slowly crosslinking formulation as a liquid embolic composition so that the embolic composition diffuses before gelation and a network or web of polymerized hydrogel is formed. In other cases, where a more compact embolization is desired close to the site of administration, it is desirable to use a more quickly crosslinking formulation.

In one embodiment, a redox initiated macromer composition is used. Using a triple lumen catheter, a solution containing the reductant is introduced through one lumen, a solution containing the oxidant is introduced using a second lumen, and the third lumen is used for introducing liquid contrast to monitor the site before and after administration of the embolic composition. The macromer can be in one or both of the reductant and oxidant solutions. Desirably, a contrast agent is present in one or both of the reductant or oxidant solutions so that administration of the embolic composition can be monitored. The uterine artery, for example, to be embolized can be accessed through the femoral artery or transcervically.

Filling Aneurysm Sacs

Many aneurysms, particularly cerebral aneurysms, can be treated endovascularly by occluding the aneurysm with the embolic composition. The embolic composition is administered using a microcatheter. Methods of administering embolic agents are known to those skilled in the art and generally can be used with the embolic composition.

In one embodiment, a redox initiated macromer composition is used, as described above for lumen embolics. It may be desirable to use a balloon, a stent, or another mechanism, for temporarily isolating the aneurysm and providing a template for embolic formation.

AAAs and TAAs are currently treated endovascularly by the placement of a stent graft at the site of the aneurysm. Often, there are leaks into the excluded aneurysm sac, termed endoleaks, due to feeder vessels into the sac, spaces between the stent graft and the vessel wall, or holes in the stent graft wall. Such endoleaks can cause the aneurysm to further expand and to rupture. The embolic compositions disclosed herein can be used to seal endoleaks. In one embodiment, the embolic compositions are used to fill the aneurysm sac.

An excluded aneurysm sac can be accessed in at least three ways: using a catheter to access the sac through the stent graft side wall; using a syringe to access the excluded sac through the patient's back; or using a catheter to access the sac through blood vessels feeding the sac. Any of theses methods can be used to administer the embolic compositions into the sac. If the endoleak is due to a feeder vessel, it may be desirable to endovascularly access the sac through the feeder vessel. Using this method, the sac can be filled and the vessel embolized, if desired. In some cases, it may be difficult to endovascularly access the sac and it may be preferable to inject embolic composition directly into the sac using a syringe through the patient's back.

It may be desirable to use a more adhesive embolic composition, which will adhere to the vessel wall within the aneurysm sac and discourage leakage between the hydrogel mass and the vessel wall.

Chemoembolization

The embolic compositions can be used for chemoembolization. As described above, a chemotherapeutic agent is incorporated into the embolic compositions or simply mixed with the preformed embolic articles. The embolic composition is then administered as described above.

For chemoembolization, as well as other applications, it may be desirable to use an embolizing composition that forms a partially or fully degradable hydrogel. Current practice calls for several applications of chemotherapeutic agent at time intervals of about 4 to 8 weeks. The embolic compositions can be formulated to degrade, partially or fully, over a desired period of time, at which time the chemoembolic composition or just the chemotherapeutic agent can be readministered. In another embodiment, embolectomy methods can be used to recannulate the embolization to allow reapplication of chemotherapeutic agent.

In another embodiment, the chemoembolic composition forms a hydrogel that releases the chemotherapeutic agent over the entire desired treatment period.

EXAMPLES

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric. The examples are not intended to restrict the scope of the invention.

Example 1

Embolization of Rabbit Renal Vasculature with Liquid Embolic Compositions

General Procedure:

Following general anaesthesia, the superficial femoral artery was surgically exposed and a microcatheter (three lumen, 3.4 Fr from ACT Medical unless otherwise noted) was introduced using a guidewire. One of the lumens was used to administer contrast agent to the animal. The microcatheter was advanced under fluoroscopic guidance to the left renal artery. The embolic composition was injected under fluoroscopic control. Following polymer injection, localization of the cured radio-opaque polymer was followed up by conducting an angiogram to assess whether complete blockage of the kidney vasculature was achieved.

The liquid embolic compositions were two part redox formulations having reductant and oxidant solutions. The macromer for all samples except F had a PVA backbone (14 kDa, 12% acetate incorporation) modified with 0.45 meq/g N-acrylamidoacetaldehyde di methyl acetal pendant polymerizable groups (about 6.3 crosslinks per chain). In Sample F, the macromer had a PVA backbone (6 kDa, 80% hydrolyzed from Polysciences) modified with 1.0 meq/g N-acrylamidoacetaldehyde dimethyl acetal and 0.5 meq/g acetaldehyde dimethyl acetal (a hydrophobic modifier). The macromers were made substantially as described in U.S. Pat. No. 5,932,674

The comonomer used was AMPS. The contrast agent was Omnipaque®. The buffer used in the oxidant solutions was IM acetate buffer, pH=4.1. None of the reductant solutions contained buffer.

TABLE 1

| | Composition Components | | | | | | | | |
|---|---|---|---|---|---|---|---|---|---|
| | A | B | C | D | E | F | G | H | I |
| Reductant Solution | | | | | | | | | |
| Fe (ppm) | 2240 | 2240 | 2240 | 2240 | 2240 | 2240 | 2240 | 2240 | 2240 |
| Ascorbate (mM) | 20.8 | 20.8 | 8.3 | 8.3 | 8.3 | 8.3 | 20.8 | 20.8 | 20.8 |
| Macromer (%) | 9 | 6 | 9 | 6 | 8 | 11.5 | 9 | 9 | 6 |
| Comonomer (%) | — | 3 | 5 | 5 | 5 | 5 | — | — | — |
| Contrast (%) | 30 | 30 | 20 | 45 | 30 | 30 | 30 | 30 | — |
| Viscosity (cp) | 33.9 | 32.6 | 33.6 | 29.3 | 33.5 | 36.7 | 34 | 32.7 | 13.5 |

TABLE 1-continued

| Composition Components | | | | | | | | | |
|---|---|---|---|---|---|---|---|---|---|
| Oxidant Solution | | | | | | | | | |
| Peroxide (ppm) | 150 | 250 | 200 | 250 | 250 | 250 | 250 | 250 | 150 |
| Buffer (mM) | 100 | 100 | 100 | 100 | 100 | 100 | 100 | 100 | 100 |
| Macromer (%) | 9 | 9 | 6 | 6 | 8 | 11.5 | 9 | 9 | 6 |
| Comonomer (%) | — | — | 3 | 5 | 5 | 5 | — | — | — |
| Dequest ® (ppm) | 100 | 100 | 100 | 100 | 100 | 100 | 100 | 100 | 100 |
| Contrast (%) | 30 | 30 | 50 | 45 | 30 | 30 | 30 | 30 | 30 |
| Viscosity (cp) | 34.6 | 32.5 | 31.0 | 29.6 | 34.6 | 36.2 | 32.8 | 33.4 | 12.9 |

| | J | K | L | M | N | O | P |
|---|---|---|---|---|---|---|---|
| Reductant Solution | | | | | | | |
| Fe (ppm) | 2240 | 2240 | 2240 | 2240 | 2240 | 2240 | 2240 |
| Ascorbate (mM) | 8.3 | 8.3 | 8.3 | 8.3 | 8.3 | 8.3 | 8.3 |
| Macromer (%) | 6 | 9 | 6 | 9 | 6 | 6 | 6 |
| Comonomer (%) | 3 | 5 | 3 | 5 | 5 | 5 | 5 |
| Contrast (%) | 30 | — | 30 | — | 30 | 30 | 30 |
| Viscosity (cp) | 16.3 | 18.3 | 14.8 | 18.2 | 17.0 | 16.7 | 16.7 |
| Oxidant Solution | | | | | | | |
| Peroxide (ppm) | 200 | 200 | 250 | 250 | 250 | 250 | 250 |
| Buffer (mM) | 100 | 100 | 100 | 100 | 100 | 100 | 100 |
| Macromer (%) | 6 | 6 | 6 | 6 | 6 | 6 | 6 |
| Comonomer (%) | 3 | 3 | 3 | 3 | 5 | 5 | 5 |
| Dequest ® (ppm) | 100 | 100 | 100 | 100 | 100 | 100 | 100 |
| Contrast (%) | 30 | 30 | 30 | 30 | 30 | 30 | 30 |
| Viscosity (cp) | 15.0 | 15.6 | 14.8 | 15.1 | 17.1 | 16.8 | 16.5 |

TABLE 2

| Results of Example 1 | | | | |
|---|---|---|---|---|
| | Injection volume (ml) | Injection time (sec) | Flow Occlusion? | In vitro gel time (sec) |
| A | 1.0 | 65 | Yes | 1.75 |
| B | 0.8 | 15 | Yes | 1.2 |
| C | 0.5 | 12 | Yes | 0.82 |
| D | 0.8 | 14 | Yes | 0.70 |
| E | 0.8 | n.d. | Yes | 0.74 |
| F | 0.5 | 12 | Yes | 0.75 |
| G | 0.5 | 10 | Yes | 1.2 |
| H | 0.9 | 14 | Yes | 1.23 |
| I | 1.4 | 45 | Yes | 2.79 |
| J | 1.6 | 45 | Yes | 1.15 |
| K | 1.4 | 20 | No | 0.87 |
| L | 1.4 | 20 | Yes | 0.79 |
| M | 1.4 | 32 | No | 0.85 |
| N | 0.8 | 17 | No | 0.68 |
| O | 3.2 | 45 | Yes | 0.85 |
| P | 1.6 | 18 | Yes | 0.79 |

The liquid embolic compositions were easily injected through the catheter and easily visualized by fluoroscopy. The compositions flowed into small distal vessels within the kidneys before gelation. By fluoroscopy, the polymer following injection was located homogenously within the renal vasculature with small arteries being filled. No polymer was seen in the renal vein for any of the samples except K, M, and N.

Example 2

Microsphere Embolic Compositions

General Method of Making Microspheres:

300 ml of 1,2-dichloroethane (DCE) or paraffin was placed into a 500 ml dented kettle and stirred with a glass stir rod. Stabilizer was added (either cellulose acetate butyrate (CAB) or dioctyl sulfosuccinate (DOS) (the percent reported is based on the amount of DCE used)) while stirring until dissolved. Once all of the stabilizer was dissolved, stirring was ceased, and nitrogen was bubbled through the solution for 10 minutes.

The macromer solution as described in Table 3 (between 10-30% solids) was placed in a 100 ml flat-bottomed flask and stirred. 0.5% potassium persulfate was added (based on amount of DCE or paraffin used) to the macromer while stirring. Once the persulfate was dissolved, nitrogen was bubbled through the solution for 5 minutes.

The macromer solution was added to the DCE or paraffin solution dropwise, while stirring at 400 rpm. Once all of the macromer solution was added, a small positive pressure of nitrogen was applied. 0.5% N,N,N,N tetramethylethylenediamine (based on amount of DCE or paraffin used) was added to the solution. The solution was lowered into an oil bath at a temperature of 55° C. and allowed to react for three hours.

After three hours, the heat was removed and stirring was continued. Once cooled, the DCE or paraffin was vacuum filtered off, and the product was washed with DCE and acetone. The product was soaked in acetone for 30 minutes, the acetone was decanted off, and the product was soaked in water for at least 30 minutes. The water was vacuum filtered off the product. The microspheres were sonicated for 30 minutes and sieved into the desired size ranges of greater than 850 microns, between 850 and 500 microns, between 500 and 250 microns, and smaller than 250 microns. The macromer used in samples A through G had a PVA backbone (14 kDa, 12% acetate incorporation) modified with 0.45 meq/g N-acrylamidoacetaldehyde dimethyl acetal pendant polymerizable groups (about 6.3 crosslinks per chain). The macromer used in sample H had a backbone of PVA 8-88 (67 kDa, 12% acetate incorporation) modified with N-acrylamidoacetaldehyde dimethyl acetal pendant polymerizable groups (about 7 crosslinks per chain). The macromer used in sample I had a backbone of PVA 4-88 (31 kDa, 12% acetate incorporation) modified with N-acrylamidoacetaldehyde dimethyl acetal pendant polymerizable groups (about 7 crosslinks per chain). The stir speed was 400 rpm except for sample G which was 350 rpm.

TABLE 3

Preparation of Microspheres

| Sample | Macromer (%) | Stabilizer | Yield (%) | Size Distribution (microns) >850 | 850-500 | 500-250 | <250 |
|---|---|---|---|---|---|---|---|
| A | 20 | 0.8% CAB in DCE | 101 | 0 | 3 | 80 | 17 |
| B | 20 | 0.5% CAB in DCE | 115 | 34 | 41 | 19 | 6 |
| C | 30 | 1% DOS in paraffin | 41 | nd | nd | nd | nd |
| D | 30 | 1% DOS in paraffin | 134 | 16 | 60 | 19 | 5 |
| E | 20 | 1% CAB in DCE | 96 | 0 | 14 | 72 | 13 |
| F | 20 | 0.8% CAB in DCE | 96 | 0 | 32 | 57 | 11 |
| G | 10 | 0.8% CAB in DCE | 96 | 3 | 0 | 22 | 76 |
| H | 11 | 0.8% CAB in DCE | 150 | 0 | 10 | 84 | 6 |
| I | 20 | 0.8% CAB in DCE | 92 | 6 | 60 | 31 | 3 |

The microsphere products had very little aggregates (except for sample D) and were mostly or all spherical.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

[1. A method for embolization, comprising the steps:

providing a composition comprising macromers having a polymeric backbone comprising units with a 1,2-diol or 1,3-diol structure and at least two pendant chains bearing crosslinkable groups and having the formula:

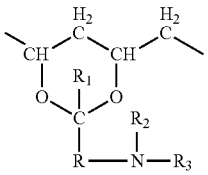

in which R is a linear or branched $C_1$-$C_8$ alkylene or a linear or branched $C_1$-$C_{12}$ alkane; $R_1$ is hydrogen, a $C_1$-$C_6$ alkyl, or a cycloalkyl; $R_2$ is hydrogen or a $C_1$-$C_6$ alkyl; and $R_3$ is an olefinically unsaturated electron attracting copolymerizable radical having up to 25 carbon atoms;

delivering the composition to the intended site of embolization, or upstream of the intended site; and then crosslinking the macromers to form a hydrogel;

wherein the crosslinkable groups of the macromer are crosslinkable via free radical polymerization that is redox initiated;

and the composition comprises a first solution comprising a reductant and a second solution comprising an oxidant and the macromers are present in either or both solutions.]

[2. The method of claim 1, wherein the macromere further comprises pendant modifier groups.]

[3. The method of claim 1, further comprising administering an active agent.]

[4. The method of claim 3, wherein the active agent is a chemotherapeutic agent.]

[5. The method of claim 1, wherein the hydrogel is biodegradable.]

[6. The method of claim 1, wherein the composition further comprises a copolymerizable monomer.]

[7. The method of claim 1, wherein the method comprises using a delivery device to deliver the solutions separately and mixing the solutions to initiate crosslinking.]

[8. The method of claim 7 wherein the solutions are delivered to the intended site using a multilumen catheter.]

[9. The method of claim 8 wherein the solutions are mixed in the catheter.]

[10. The method of claim 1, wherein the embolization is used for treatment of a uterine fibroid, by delivering the embolic composition to a vessel feeding the fibroid to occlude the vessel.]

[11. The method of claim 1, wherein the embolization is used for treatment of a tumor, by delivering the embolic composition to a vessel feeding the tumor to occlude the vessel.]

[12. The method of claim 1, wherein the embolization is used for treatment of an endoleak by delivering the embolic composition to seal the endoleak.]

[13. The method of claim 12, wherein sealing the endoleak comprises partially or completely filling the aneurysm sac with the embolic composition.]

[14. The method of claim 1, wherein the embolization is used for treatment of an arteriovenous malformation by delivering the embolic composition to occlude the malformation.]

*15. A method of treating an animal, comprising:*

*providing a composition comprising macromers having a polymeric backbone comprising units with a 1,2-diol or 1,3-diol structure and at least two pendant chains bearing crosslinkable groups and having the formula:*

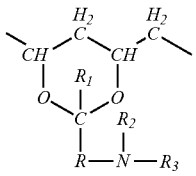

*in which R is a linear or branched $C_1$-$C_8$ alkylene or a linear or branched $C_1$-$C_{12}$ alkane; $R_1$ is hydrogen, a $C_1$-$C_6$ alkyl, or a cycloalkyl; $R_2$ is hydrogen or a $C_1$-$C_6$ alkyl; and $R_3$ is an olefinically unsaturated electron attracting copolymerizable radical having up to 25 carbon atoms;*

*delivering the composition to the animal to partially or totally block or fill a lumen, space, or cavity; and*

*crosslinking the macromers to form a hydrogel;*

*wherein the crosslinkable groups of the macromer are crosslinkable via free radical polymerization that is redox initiated; and*

*wherein the composition comprises a first solution comprising a reductant and a second solution comprising an oxidant and the macromers are present in either or both solutions.*

*16. The method of claim 15 wherein the composition is delivered to block or fill a lumen.*

*17. The method of claim 15 wherein the composition is delivered to block or fill a space.*

*18. The method of claim 15 wherein the composition is delivered to block or fill a cavity.*

*19. The method of claim 15, wherein the macromer further comprises pendant modifier groups.*

*20. The method of claim 15, wherein the composition includes an active agent.*

*21. The method of claim 15, wherein the hydrogel is biodegradable.*

*22. The method of claim 15, wherein the composition further comprises a copolymerizable monomer.*

*23. The method of claim 15, wherein the method comprises using a delivery device to deliver the solutions separately and mixing the solutions to initiate crosslinking.*

*24. The method of claim 15, wherein the solutions are delivered to the intended site using a multilumen catheter.*

*25. The method of claim 15, wherein the solutions are mixed in the catheter.*

*26. The method of claim 15, wherein the solutions are delivered to the intended site using a syringe.*

* * * * *